(12) United States Patent
Starnes (10) Patent No.: US 8,133,246 B1
(45) Date of Patent: Mar. 13, 2012

(54) SAFETY LANCET ASSEMBLY

(75) Inventor: Charles D. Starnes, Coral Springs, FL (US)

(73) Assignee: Caribbean Medical Brokers, Inc., Coral Springs, FL (US)

( * ) Notice: Subject to any disclaimer, the term of this patent is extended or adjusted under 35 U.S.C. 154(b) by 1299 days.

(21) Appl. No.: 10/896,691

(22) Filed: Jul. 22, 2004

Related U.S. Application Data (60) Provisional application No. 60/563,042, filed on Apr. 16, 2004.

(51) Int. Cl.
*A61B 17/32* (2006.01)

(52) U.S. Cl. ........................................ 606/182

(58) Field of Classification Search .......... 606/181–186, 606/188; 600/583
See application file for complete search history.

(56) References Cited

U.S. PATENT DOCUMENTS

| | | | |
|---|---|---|---|
| 2,270,655 A * | 1/1942 | Keeran .............................. | 30/162 |
| 2,838,049 A * | 6/1958 | Eisenhofer et. al. ........... | 606/167 |
| 3,358,689 A | 12/1967 | Higgins | |
| 4,192,066 A * | 3/1980 | Tucker ............................ | 30/162 |
| 4,469,110 A * | 9/1984 | Slama ........................... | 600/583 |
| 4,503,856 A * | 3/1985 | Cornell et al. ................ | 606/182 |
| 4,677,979 A | 7/1987 | Burns | |
| 4,895,147 A * | 1/1990 | Bodicky et al. ............... | 606/182 |
| 5,100,427 A | 3/1992 | Crossman et al. | |
| 5,207,699 A | 5/1993 | Coe | |
| 5,324,303 A * | 6/1994 | Strong et al. .................. | 606/181 |
| 5,370,654 A * | 12/1994 | Abidin et al. ................ | 606/182 |
| 5,385,571 A | 1/1995 | Morita | |
| 5,423,847 A | 6/1995 | Strong et al. | |
| 5,431,672 A * | 7/1995 | Cote et al. ..................... | 606/167 |
| 5,439,473 A | 8/1995 | Jorgensen | |
| 5,487,748 A | 1/1996 | Marshall et al. | |
| 5,545,175 A * | 8/1996 | Abidin et al. ................. | 606/182 |
| 5,554,166 A | 9/1996 | Lange et al. | |
| 5,575,804 A * | 11/1996 | Yoon ............................. | 606/185 |
| 5,628,764 A | 5/1997 | Schraga | |
| 5,628,765 A | 5/1997 | Morita | |
| 5,645,557 A * | 7/1997 | Yoon ............................. | 606/185 |
| 5,749,886 A * | 5/1998 | Abidin et al. ................. | 606/182 |
| 5,755,733 A | 5/1998 | Morita | |
| 5,873,887 A | 2/1999 | King et al. | |
| 5,984,940 A | 11/1999 | Davis et al. | |
| 5,993,470 A * | 11/1999 | Yoon ............................. | 606/185 |
| 6,090,124 A | 7/2000 | Weekes | |
| 6,106,537 A * | 8/2000 | Crossman et al. ............ | 606/181 |
| 6,156,051 A | 12/2000 | Schraga | |
| 6,258,112 B1 | 7/2001 | Schraga | |
| 6,432,120 B1 | 8/2002 | Teo | |

(Continued)

FOREIGN PATENT DOCUMENTS

DE 103 12 357.1 * 11/2003

*Primary Examiner* — Tuan Nguyen
*Assistant Examiner* — Thomas McEvoy
(74) *Attorney, Agent, or Firm* — Thomas C. Saitta (57) ABSTRACT

Disclosed is a safety lancet assembly configured to pierce a patient's skin. The safety lancet comprises a housing and a lancet disposed with the housing. The lancet includes both a block and a piercing tip attached to the block. The lancet is disposed within the housing such that the lancet may move from a retracted position to the piercing position. Additionally, the safety lancet includes a use indicator to alert a user or patient if the lancet is currently in the retracted position or if the lancet has been previously released to the piercing position.

18 Claims, 10 Drawing Sheets

U.S. PATENT DOCUMENTS

| | | |
|---|---|---|
| 6,514,270 B1 | 2/2003 | Schraga |
| 6,537,292 B1 | 3/2003 | Lee |
| 7,201,760 B2 * | 4/2007 | Masury et al. ............... 606/167 |
| 7,235,056 B2 * | 6/2007 | Duchon et al. ............... 600/583 |
| 7,273,484 B2 * | 9/2007 | Thoes et al. ............... 606/181 |
| 2002/0169470 A1 * | 11/2002 | Kuhr et al. ............... 606/182 |
| 2004/0249406 A1 * | 12/2004 | Griffin et al. ............... 606/182 |
| 2004/0260325 A1 * | 12/2004 | Kuhr et al. ............... 606/181 |

* cited by examiner

SAFETY LANCET ASSEMBLY

REFERENCE TO RELATED APPLICATION

Priority to the filing date of U.S. provisional patent application Ser. No. 60/563,042 filed on Apr. 16, 2004 and titled Improved Single Use Lancet Assembly is hereby claimed and which is incorporated by reference herein in its entirety.

BACKGROUND OF THE INVENTION

1. Technical Field

The present invention relates in general to the field of medical lancet devices and self-contained single use lancing devices that enable user safety and security. More particularly, the invention relates to lancing devices containing the lancet needle permanently affixed within the lancing device, providing a safety guard to prevent unintended activation and release of the lancet needle, and providing an indicator within the unit for identifying whether or not the lancing device has been previously activated, used and spent. Additionally, the invention relates to providing a method of indicating and assuring that lancing devices are limited to one-time use only. Specifically, the invention provides a method for indicating whether the lancing device has been activated and the lancet needle ejected from the device and then retracted.

2. Description of the Related Art

Lancets and their uses are well known in the art as a convenient and safe means for piercing or pricking a person's skin to draw small amounts blood that can then be subjected to a variety of medical tests such as for blood sugar content. Typical integrated lancet assemblies are described in U.S. Pat. Nos. 5,439,473 and 6,258,112 and depict a lancet encased within a rectangular-shaped plastic casing. The lancet contains a needle tip and is mounted in the casing in a manner that, through the use of a spring, enables the lancet to be retracted, actively released by the user, and consequently propelled linearly toward one end of the casing. Upon reaching the end of the casing, the needle tip of the lancet extends through a small opening in the casing thereby exposing the needle tip for the purpose of puncturing human skin, such as a fingertip, positioned adjacent to the opening. The spring and lancet are released by pressing on a button or tab. Following activation and extension of the needle tip through the casing opening, the natural state of the spring causes the lancet to partially retract towards its previous state, with the spring and lancet at rest such that the needle tip no longer extends through the casing opening.

Lancets are designed to draw a relatively minute quantity of blood from capillaries immediately below the surface of the skin and are commonly used by the patients themselves at home as well as by medical professionals in medical offices and hospitals. Lancets are used to prick the patient's skin either by manual penetration or in conjunction with a dynamic (usually spring-driven) mechanical device into which the lancet is permanently installed for single use. In the home setting, single use lancing devices are used by the patient and then discarded. These devices are also used in medical office and hospital settings in order avoid the necessity of having to re-sterilize the mechanical device and/or lancet after each use. Other types of lancing devices enable the user to insert, remove and replace lancets after each use. The lancing device is reusable and the lancets themselves are discarded. Single use lancets provide the convenience of enabling the user to discard the entire device and not touch, contaminate or otherwise expose the lancet or inside of the device in a manner that may comprise sterility.

Singe use lancing devices are specifically designed to safely accommodate their purpose as "pricking" devices that are commonly utilized by non-medically trained individuals including children. Specifically, in order to effectuate a safe and controlled puncturing of a patient's skin, the exposed tip of the needle extends only a very short distance (typically a few millimeters) from the flat upper surface of the lancet body, which acts as a bearing to limit the puncture depth. The needle may extend from the upper surface using any well-known lancet configurations, such as by having the needle protrude outward from the lancet body or by otherwise affixing the needle to the upper surface. Together, these signature structural and dimensional characteristics of lancet design give rise to another nearly universal lancet design feature, namely, a single unitary molded plastic device that may be fired once for releasing the lancet needle and pricking the patient's skin surface. After use, the needle remains stored within the casing. The unit may be re-cocked and re-used by using a key to re-compress the spring.

A problem arises, however, concerning safety after a lancing device has been used to draw blood. After the device has been used to prick the patient's skin, the sharp lancet tip is contaminated with the patient's blood. The outer surface of the unit makes contact with the patient's skin and may also be contaminated. Additionally, the needle, retracted back within the unit after use, contains blood that may contaminate the interior of the unit. As with any instrument or device that has been exposed to blood, a used lancing device constitutes a significant biological hazard that must be handled with care.

However, the nature and shape of the lancing devices presents difficulties relating to a user's ability to identify a used device therefore to distinguish a used from an unused lancing unit. A user may only determine whether the device has been used by depressing the activation switch again. By depressing the switch again, the unit will either: (1) not respond, meaning the unit was previously used and should be discarded; or (2) it will activate and fire the needle, thereby spending the unit without any practical use and requiring that it then be discarded. Thus, there is no simple, efficient and practical method of making this determination in advance of the lancing device's use.

Since lancing devices are commonly stored in bags or boxes of more than fifty, the inability to readily and reliably distinguish between used and unused lancing devices creates significant health and safety problems in which contaminated devices may be used and then replaced into the storage bag among unused devices without the knowledge of the next user. Given the many prevalent blood-borne diseases such as hepatitis, a single such misidentification is potentially catastrophic. Additionally, federal regulations and requirements of the health care industry, such as Medicare, contain provisions that medical and heath providers cannot use or stock returned lancet inventory without definite certainty that the returned items have not been tampered with or used.

It can therefore be appreciated that a need exists for an improved lancing design that overcomes the foregoing problems associated with the inability to determine whether a lancing device is spent.

SUMMARY

The present invention relates generally to a safety lancet assembly configured to pierce a patient's skin. The safety assembly lancet comprises a housing and a lancet disposed with the housing. The lancet includes both a block and a piercing tip attached to the block. The lancet is disposed within the housing such that the lancet may move from a retracted position to a piercing position. Additionally, the safety lancet includes a use indicator to alert a user or patient if the lancet is currently in the retracted position or if the lancet has been previously released to the piercing position.

In greater detail, the safety lancet assembly includes a first and second indicator panel. The indicator panels may have any various geometric shapes or configurations such as circles, squares, rectangles or three dimensions shapes such as raised panels and dots. Typically, the first and second indicator panels are operatively located below an indicator window formed within the housing when the lancet is in the retracted position. The first indicator panel may be connected to the block and is visible through the indicator window while obscuring the second indicator panel from view when the lancet is in the retracted position. The second indicator panel is visible through the indicator window when the lancet has been moved to the piercing position.

Furthermore, the safety lancet assembly includes a driving assembly having a biasing element such as a spring operatively disposed between the lancet and the housing. Additionally, an actuator assembly is included for releasing the lancet from the retracted position. Typically, the actuator assembly comprises a release tab operatively connected to the block of the lancet so as to retain the lancet in the retracted position. The safety lancet assembly may also include a guard operatively connected to both the housing and the actuator assembly for preventing the accidental release of the actuation assembly.

The invention, as well as a preferred mode of use, further objects and advantages thereof, will best be understood by reference to the following detailed description of an illustrative embodiment when read in conjunction with the accompanying drawings.

DETAILED DESCRIPTION

A full and enabling disclosure of the present invention, including the best mode known to the inventor of carrying out the invention is set forth more particularly in the remainder of the specification, including reference to the accompanying drawings, wherein like reference numerals designate corresponding parts throughout several figures. This description is made for the purpose of illustrating the general principles of the invention and should not be taken in the limiting sense.

FIGS. 1-10 illustrate a safety lancet assembly according to the present invention. The safety lancet 1 has an elongate lancet housing 2. The lancet housing 2 may be rectangularly shaped as depicted, with two long ends. However, the lancet housing may take the form of most any shape, such as a cylinder or box. The lancet housing 2 depicted in the Figures has a first end 3 with an opening 4 and a second end 5 having a wall portion 6 and may also have an opening.

The interior of lancet housing 2 accommodates a movable block 7 that is movable longitudinally within lancet housing 2 between first end 3 and second end 5. Movable block 7 has a first end 16 nearest to first end 3 of lancet housing 2, and second end 17 nearest to second end 5. Movable block 7 comprises a needle 8 extending from first end 16. Needle 8 contains a needle tip 9 at its end and are positioned on first end 16 to be in communicable alignment with opening 4 such that when the first end 16 is flush against first end 3 of lancet housing 2, needle 8 and needle tip 9 extend through opening 4. Second end 17 of movable block 7 contains a knobbed portion 10 extended therefrom. The knobbed portion 10 faces second end 5 of lancet housing 2. Lancet housing 2 and block 7 may be manufactured using one or more of a variety of suitable materials such as semi-rigid plastics, which are suitable for manufacturing using well-known injection molding manufacturing techniques. Likewise needle 8 may be of any type of material known in the art, such as stainless steel.

Block 7 also contains an upper side 11, a lower side 12 and opposing sides 13. Opposing sides 13, are depicted as 13a and 13b. Opposing sides 13 contain a catch 14. Catch 14 may be located either on both opposing sides 13 or there may only be one catch located on either side 13a or 13b. Catch 14 is located in close proximity to second end 17 of block 7. Upper side 11 of movable block 7 also contains indicator cover 15 that extends outward from second end 17 and above knobbed portion 10. Indicator cover 15 (or first indicator panel) may be attached to upper side 11 or the top portion of second end 17. Indicator cover 15 may also be integrally molded as a single piece with block 7.

Lancet housing 2 has a top surface 18 having an indicator opening or indicator window 19 and a release tab 20. Indicator opening 19 is located towards second end 5 of lancet housing 2 and contains an opening into the interior of lancet housing 2. Below indicator opening 19 and within the interior of lancet housing 2 is a second indicator (or second indicator panel) 21 that extends from the second end 5 of lancet housing 2. Second indicator 21 and indicator opening 19 are positioned in such a manner that the top surface of second indicator 21 is clearly visible through indicator opening 19 when the view is unobstructed. Second indicator 21 and indicator opening 19 are spaced apart to create a gap that may form a slot or shelf for slidably receiving indicator cover 15. Indicator cover 15 is received within this gap when movable block 7 is positioned in a retracted position. When block 7 is in a retracted position, indicator cover 15 eclipses the view of second indicator 21 and only the top surface of indicator cover 15 is visible through indicator opening 19. When block 7 is not retracted, indicator cover 15 is forward of the gap and the top surface of second indicator 21 is exposed and viewable through indicator opening 19. In combination, indicator cover 15, second indicator 21 and opening 19 act as a use indicator. In the preferred embodiment, the top surfaces of indicator cover 15 and second indicator 21 are different colors such that a safety lancet user can easily look into indicator opening 19 and readily determined whether or not movable block 7 is in the retracted position based upon the visible color.

Also located within the interior of lancet housing 2 is a driving assembly having a biasing element, such as a spring operatively disposed between the lancet and the housing, for moving movable block 7 and needle 8 between the retracted position and the piercing position. Spring 22 is positioned between second end 5 of lancet housing 2 and second end 17 of movable block 7. One end of spring 22 receives knobbed portion 10 for securing spring 22 to movable block 7. The other end of spring 22 may be fastened to the interior of second end 5 using any conventional means, such as the use of a slot or partial divider for holding one of the end coils of spring 22 or an aperture for receiving an end tip of spring 22. The surface of the floor of the interior of lancet housing 2 may also contain a protruding stop 23 positioned between second end 5 and second end 17 for purposes of preventing movable block 7 from being positioned too close to second end 5 and over-compressing spring 22 and causing damage or compromising compression strength.

Lancet housing 2 also includes an actuation assembly for releasing block 7 and needle 8 from the retracted position. In the preferred embodiment, the actuation assembly includes release tab 20 extending outward of the top surface of lancet housing 2 and extending into the interior. Lancet housing 2 contains an opening about its top and side to permit release tab 20 to be received into the interior and to enable its movement in a rocking manner and serve as a switch, release or button. Release tab 20 has one or more arms 25 that extend downward into the interior of lancet housing 2. Release tab 20 may either be attached to lancet housing 2 in a manner that permits it to pivot, rock or move about a point, or it may be integrally molded with lancet housing 2 as a single piece in such a manner as to provide flexibility and movement. Arms 25 form a point 26 at their ends and extend into the interior of Lancet Housing 2 and around sides 13 of block 7.

Figure 1:
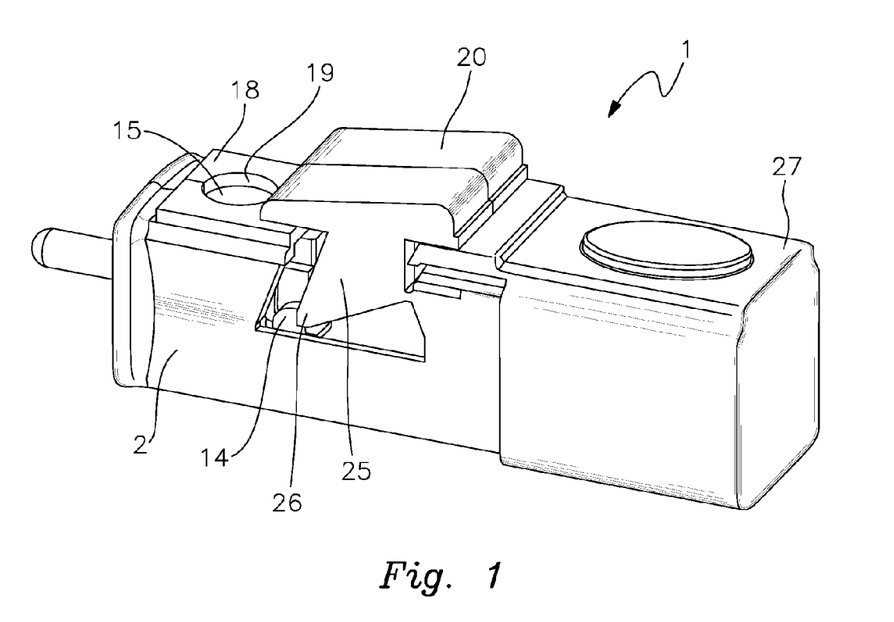
FIG. 1 illustrates an improved single use lancet assembly as manufactured prior to usage in accordance with one embodiment of the present invention.
Figure 2:
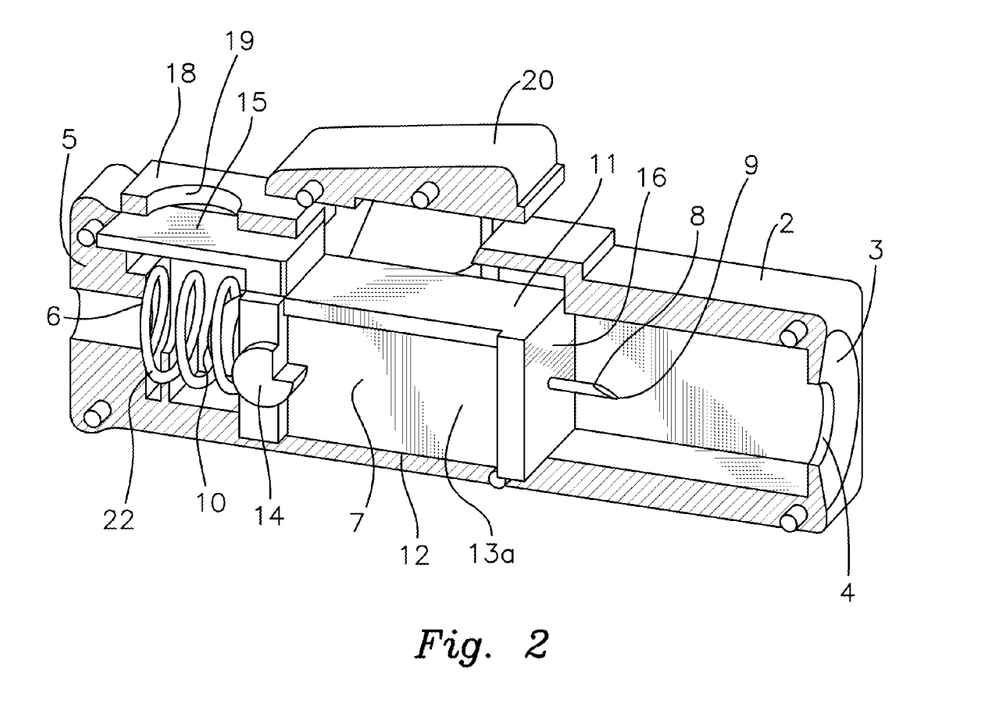
FIG. 2 depicts a side sectional view of the improved single use lancet assembly shown in FIG. 1 in the retracted position and with the guard detached.

When safety lancet 1 is in its retracted position, as depicted in FIGS. 1 and 2, movable block 7 is positioned as close to second end 5 as possible and spring 22 is compressed. In this position, each point 26 is seated within each corresponding catch 14, thereby holding movable block 7 in the retracted position and countering the force of spring 22 and its attempt to decompress and return to its natural state of equilibrium. Point 26 is depicted within catch 14 in FIG. 1. Lancing device 1 may be set into the retracted position by inserting a key (not shown) into opening 4 and applying force to first end 16 of block 7, thereby compressing spring 22. In this manner, block 7 is pushed as far back as possible until second end 17 makes contact with stop 23, or the desired distance is otherwise reached. Release tab 20 is then pressed in a manner that causes each point 26 to rest within each corresponding catch 14 thereby holding and maintaining block 7 in the retracted position. The key should be small enough to fit within opening 4 and should be configured in a manner that it pushes block 7 towards second end 5 by making contact with the surface of first end 16 but without making contact or significant contact with needle 8 to prevent contamination and deforming needle tip 9. For example, the key may constitute a long tube with an opening for receiving needle 8 within the tube's hollow cavity whereby the edges of tube make contact with end 16 of block 7. The length of the tube cavity is greater than the length of needle 8 to prevent needle tip 9 from making contact with the far wall of the key's hollow cavity.

In the retracted position, indicator cover 15 is positioned within the gap formed between second indicator 21 and indicator opening 19 such that the top surface of indicator cover 15 is visible through indicator opening 19. Point 26 is held in catch 14 thereby maintaining spring 22 in its compressed form. Safety lancet 1 remains in the retracted position until release tab 20 is activated by applying pressure to one end of its upper surface. The top surface of release tab 20 may have grooves or a tacky surface to enable gripping and movement with a single finger.

Figure 3:
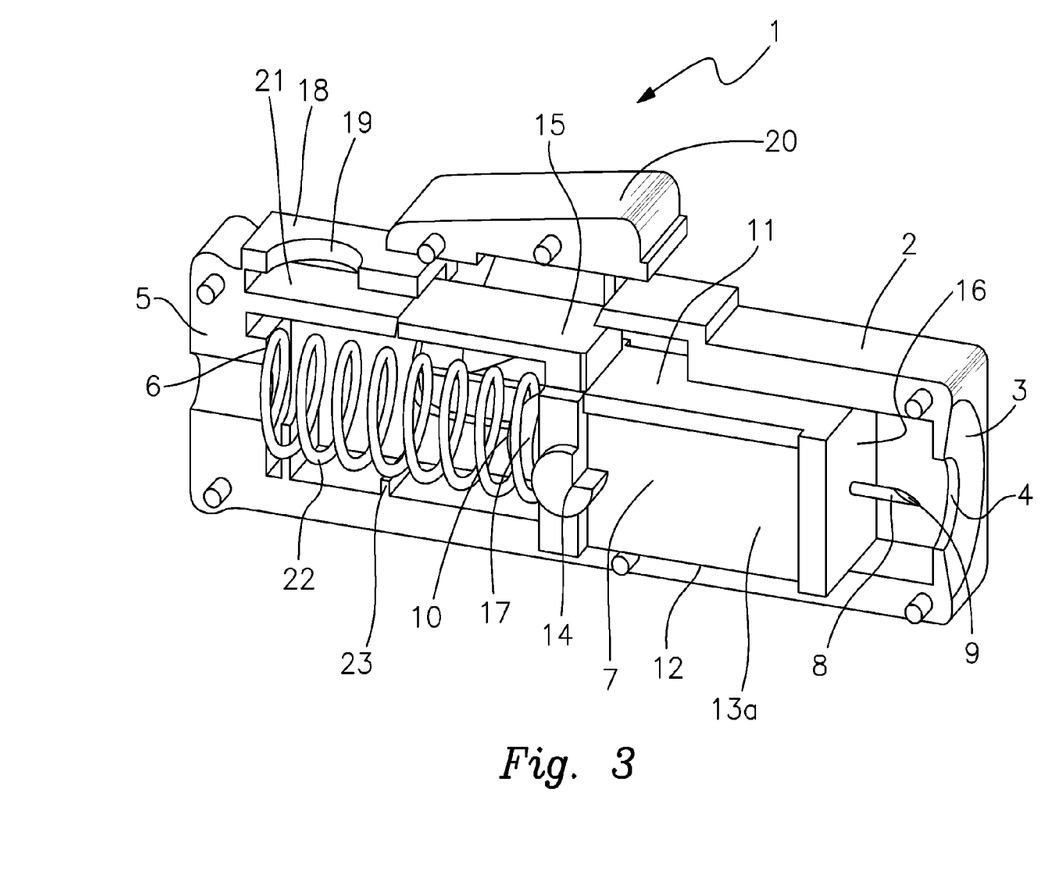
FIG. 3 depicts a side sectional view of the improved single use lancet assembly shown in FIGS. 1 and 2 following activation of the lancet to the piercing position and with the spring in equilibrium.
Figure 4:
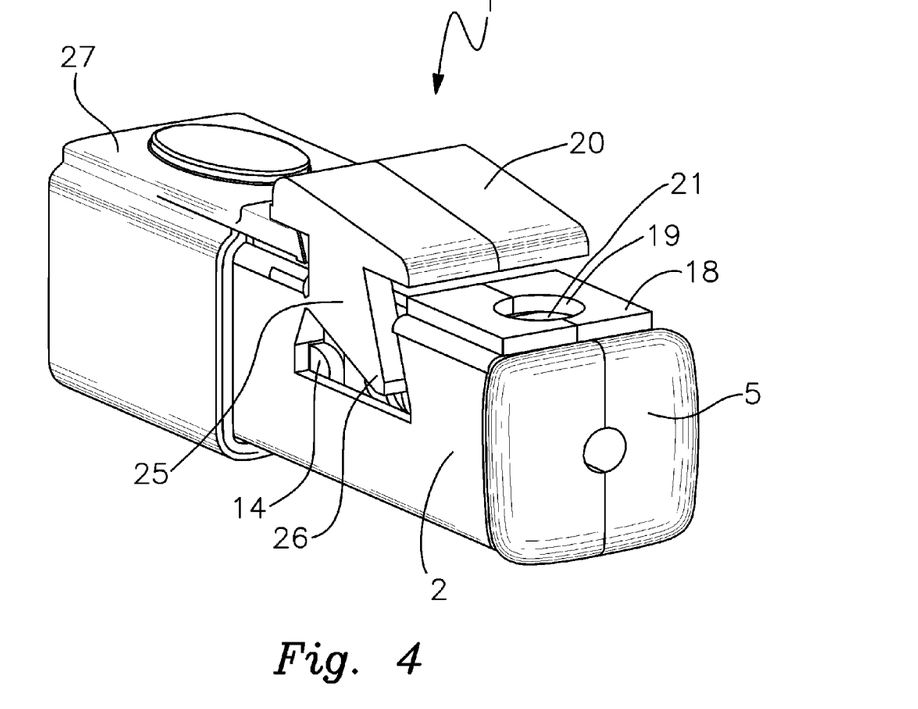
FIG. 4 illustrates a perspective view of the safety lancet assembly including a guard attached to the piercing end of the housing.
Figure 5:
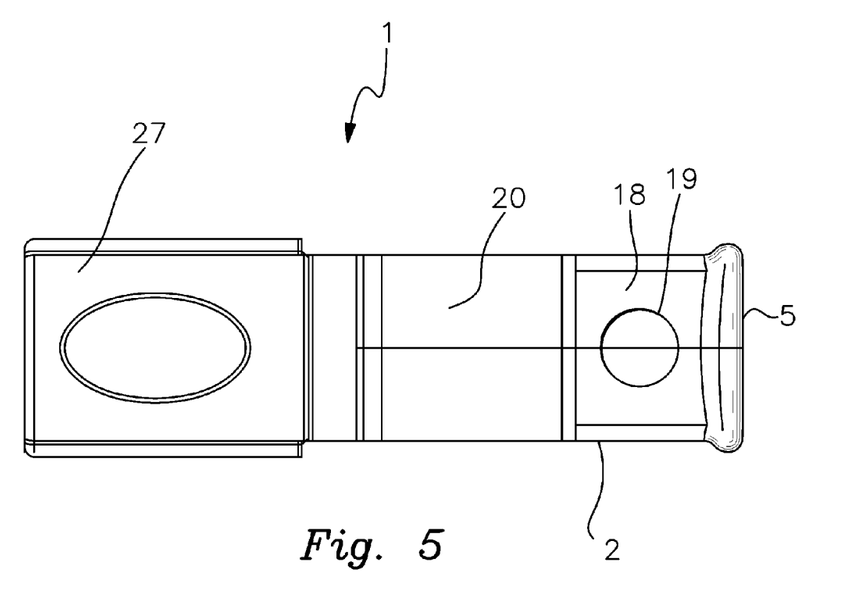
FIG. 5 shows a top view of the safety lancet assembly.
Figure 6:
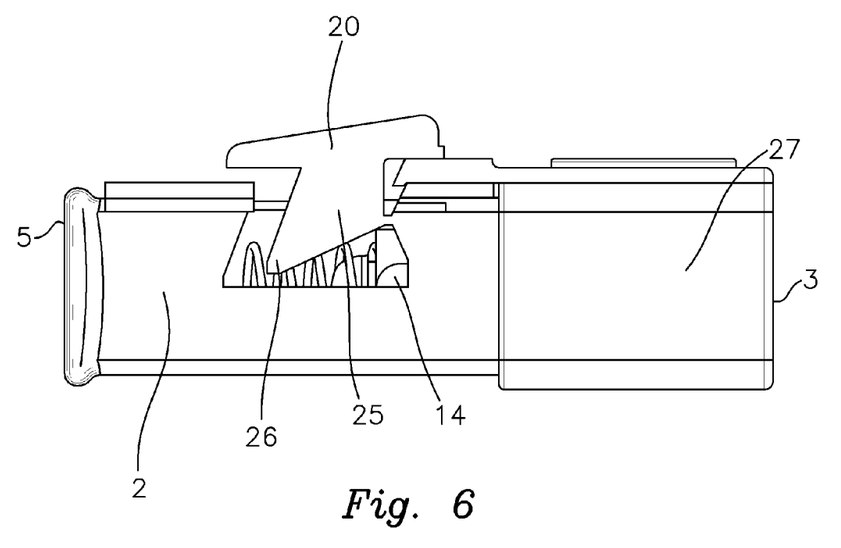
FIG. 6 depicts a side view of the safety lancet assembly showing guard and tab arrangement.
Figure 7:
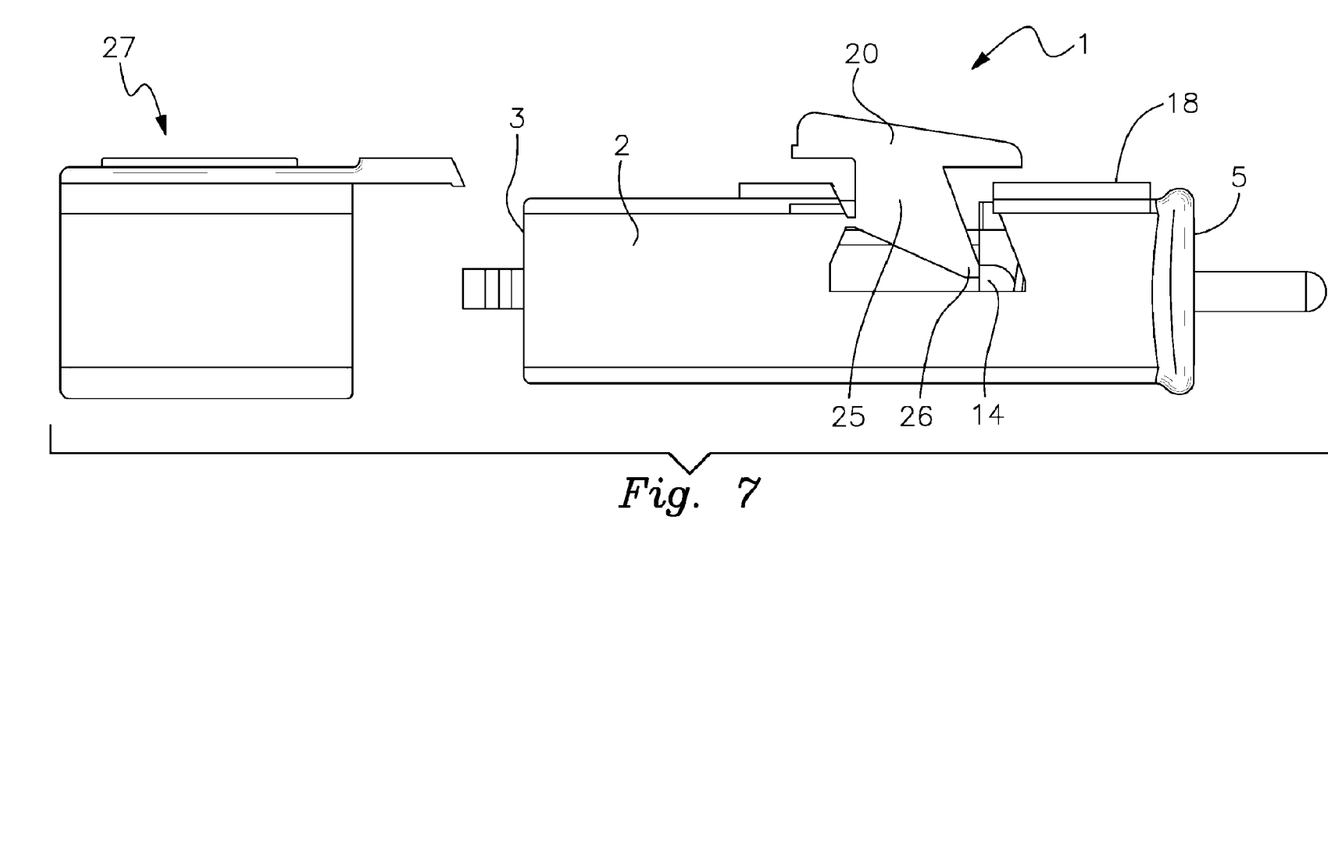
FIG. 7 illustrates an expanded view of the safety lancet assembly.

Safety lancet 1 is activated by the actuation assembly when one end of release tab 20 is pressed downward thereby causing each arm 25 to transversely move upward and raise corresponding point 26 out of each catch 14. The top surface of catch 14 may be rounded to aid in the release of point 26 to prevent catching of point 26 in the event release tab 20 is not depressed with sufficient force. Upon release, the kinetic energy of spring 22 is released and block 7 is pushed forward towards first end 3. Spring 22 expands beyond its point of equilibrium causing first end 16 of block 7 to make contact with first end 3 of lancet housing 2. Needle 8 extends outward of opening 4 so that needle tip 9 can puncture the user's skin. Spring 22 then returns to its state of equilibrium wherein block 7 is pulled back towards end 5 of lancet housing 2 and needle 8 is drawn back into the interior of lancet housing 2 and completely retracted from opening 4. At rest from its maximally expanded position, needle 8 remains completely within the interior of lancet housing 2 thereby fully preventing accidental contact of needle tip 9 with any person handling safety lancet 1 after use. Likewise, when spring 22 reaches equilibrium, indicator cover 15 is displaced away from second end 5 and no longer in the gap formed by indicator opening 19 and second indicator 21. Consequently, in this position, referred to as the piercing position, the top surface of second indicator 21 is fully exposed and visible through indicator opening 19. FIG. 3 depicts a spent safety lancet 1 with the top surface of second indicator 21 visible through indicator opening 19. In the preferred embodiment, the top surface of second indicator 21 is colored red and the top surface of indicator cover 15 is colored green. In this configuration, indicator opening 19 is visible as green when safety lancet 1 is in the retracted position and ready for one-time use, and displays red after activation. The color red serves as an indicator that safety lancet 1 has been expended and should be discarded. Users are not provided with the key for re-cocking so safety lancet 1 cannot readily be re-used.

Figure 8:
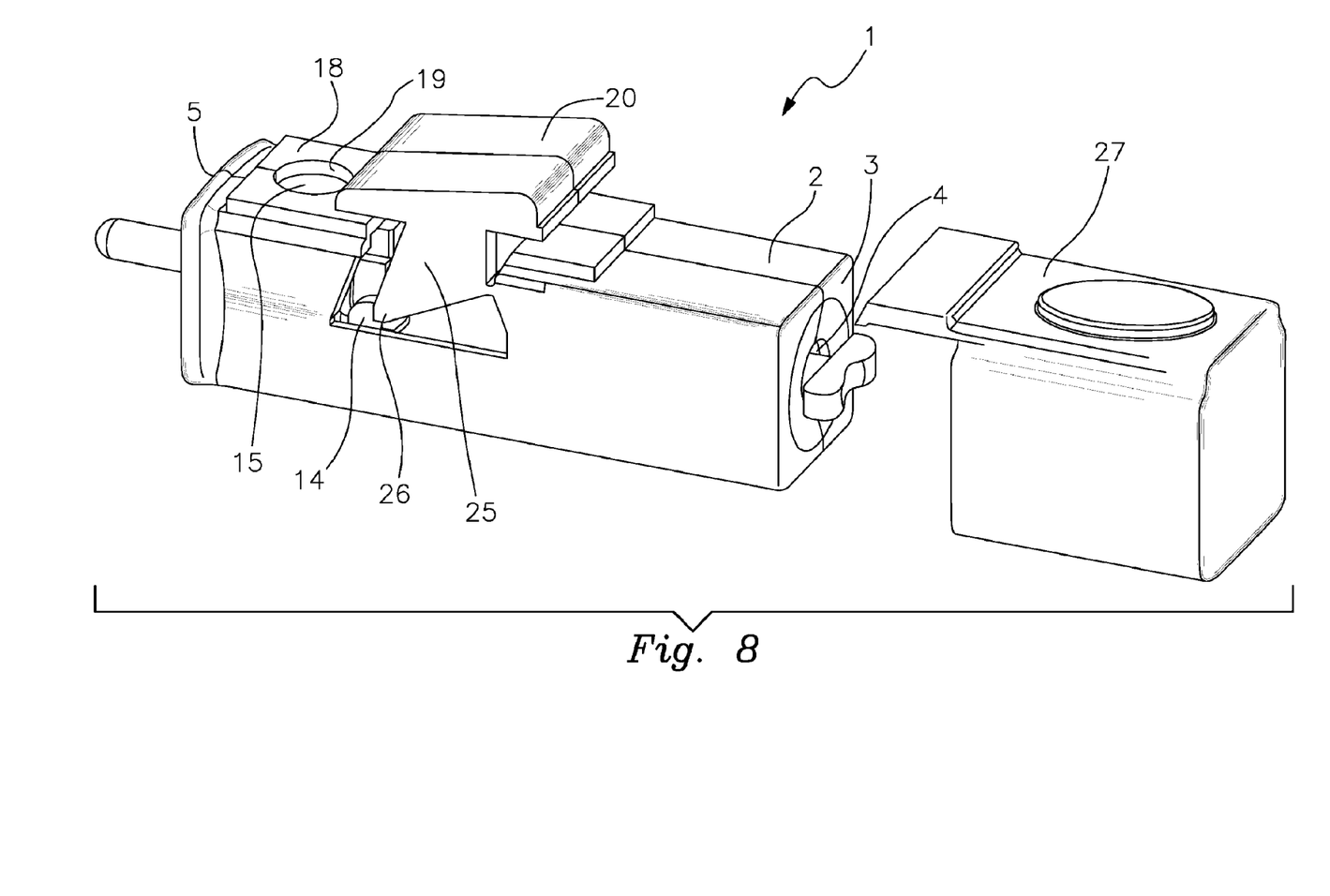
FIG. 8 depicts a further perspective view of the expanded safety lancet assembly.
Figure 9:
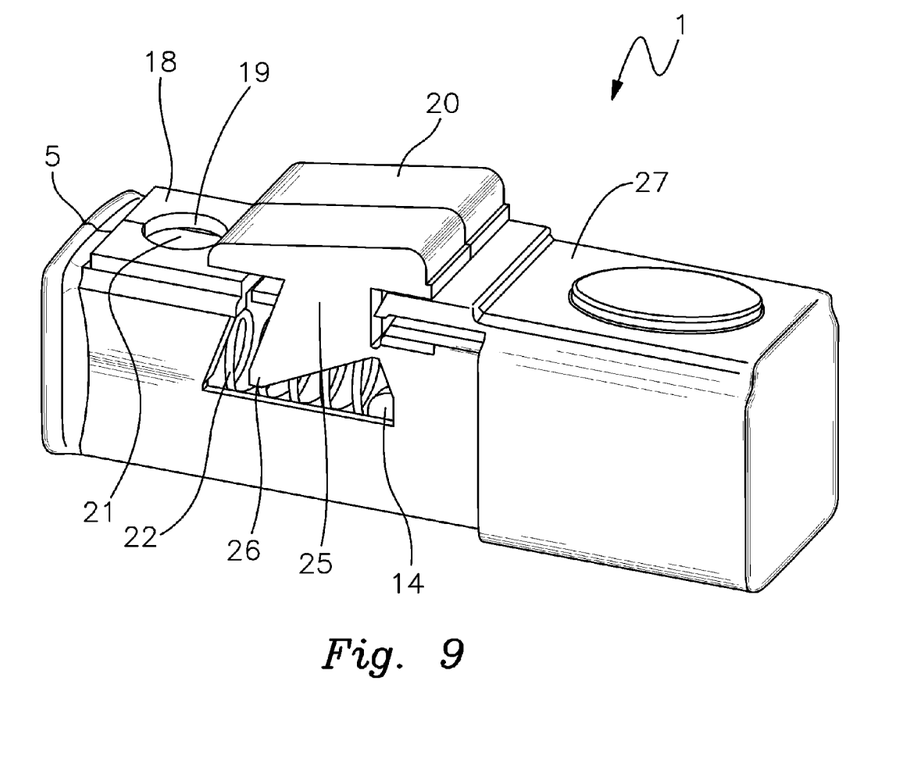
FIG. 9 illustrates an additional perspective view of the safety lancet assembly.
Figure 10:
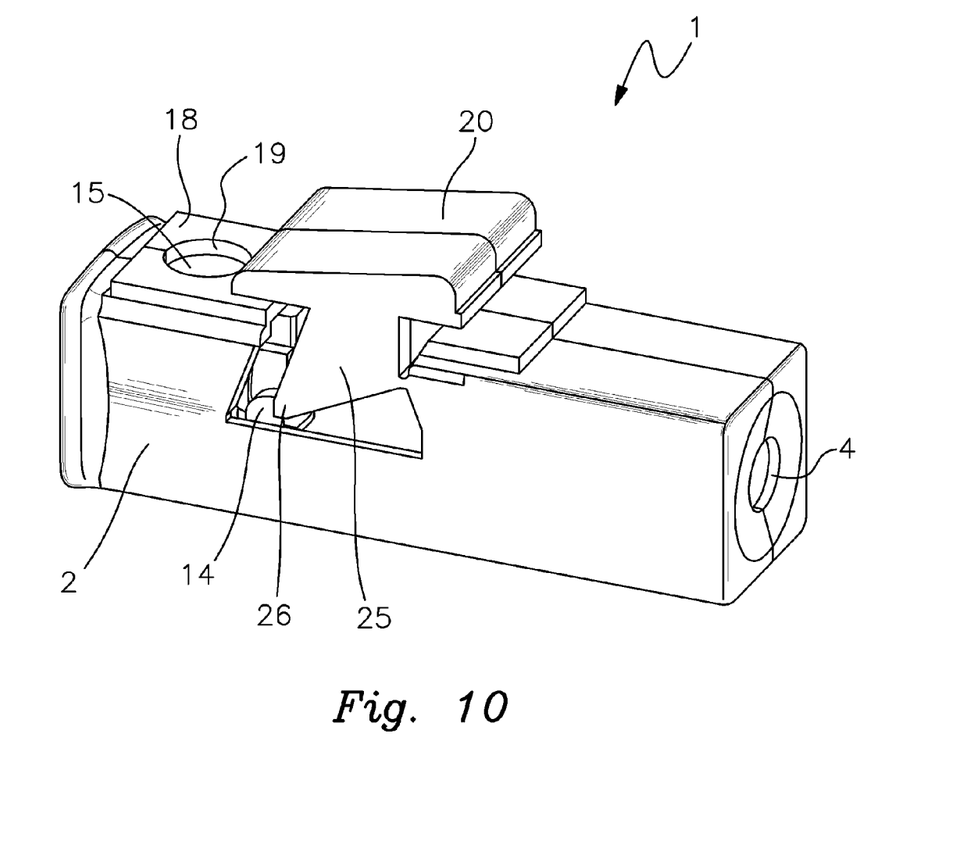
FIG. 10 shows the interaction between the arm of the release tap and the catch which form the actuator assembly of the safety lancet.

For additional safety and security, guard 27 may be inserted between the top surface of lancet housing 2 and the bottom surface of release tab 20. In this configuration, guard 27 serves as a trigger guard preventing the unintentional pressing of release tab 20 and subsequent accidental activation and release of needle 8. The use of guard 27 also prevents accidental firing of safety lancet 1 during packaging, shipment, delivery and unpacking of the units. Guard 27 can be of any shape provided it is removably positioned below release tab 20 and blocks activation. FIG. 1 depicts the preferred embodiment where guard 27 is a hollow rectangular cover that slips over the front end of lancet housing 2 and an extension of guard 27 extends beyond the rectangular cover and slides into the area between release tab 20 and the top surface of lancet housing 2. This extension may be of greater thickness than the other components of guard 27. Guard 27 may also contain one or more grooves or a tacky surface for gripping with a user's fingers. The end of guard 27 that covers end 3 of lancet housing 2 may either be open or completely closed. As depicted in FIG. 1, when guard 27 is open, such that opening 4 is visible and open when guard 27 is affixed to lancet housing 2. FIG. 8 depicts guard 27 having a closed end, such that opening 4 is not visible when guard 27 is affixed to lancet housing 2. In this latter embodiment, the covered end protects a user from being accidentally pricked by needle tip 9 should needle tip 8 unintentionally fire from opening 4.

While this invention has been described in terms of several embodiments, it is contemplated that alterations, permutations, and equivalents thereof will become apparent to one of ordinary skill in the art upon reading this specification in view of the drawings supplied herewith. It is therefore intended that the invention and any claims related thereto include all such alterations, permutations, and equivalents that are encompassed by the spirit and scope of this invention.

What is claimed is:

1. A safety lancet assembly comprising:
    a housing;
    a lancet including a block and a piercing tip attached to the block;
    the lancet disposed within the housing and operatively aligned to move at least from a retracted position wherein the lancet is completely enclosed by the housing to a piercing position wherein a portion of the lancet temporarily extends from the housing;
    a driving assembly for moving the lancet from the retracted position to the piercing position, said driving assembly comprising a biasing element operatively disposed between the lancet and the housing, wherein said biasing element propels said lancet from the retracted position to the piercing position and then pulls said lancet back into the housing such that said lancet is again completely enclosed by the housing;
    said housing comprising an actuation assembly structured to actuate said driving assembly to release the lancet from the retracted position, said actuation assembly being pivotable relative to the remainder of said housing, said actuation assembly comprising in combination an outwardly extending release tab and a pair of inwardly extending arms, said arms abutting said lancet block and precluding movement of said lancet block from said retracted position until said actuation assembly is activated by pivoting said release tab relative to the remainder of said housing such that said arms pivot away from and no longer abut said lancet block, thereby allowing said biasing element to move said lancet from said retracted position to said piercing position; and
    a use indicator, said use indicator visually indicating whether said lancet has been released from the retracted position wherein after said lancet is released by said actuation assembly from said retracted position and pulled back into said housing such that said lancet is again completely enclosed by the housing, further movement of said lancet by said actuation assembly is preclude;
    said housing including a window; and
    said use indicator including a first and second indicator panel, wherein the first and second indicator panels are located directly below the window when the lancet is in the retracted position and the first indicator panel substantially obscures the second indicator panel from view in the window when the lancet is in the retracted position.

2. The safety lancet assembly of claim 1, wherein the surfaces of the first and second indicator panels visible through the indicator window are different colors.

3. The safety lancet assembly of claim 1, wherein the surfaces of the first and second indicator panels visible through the indicator window are distinguishable.

4. The safety lancet assembly of claim 1, wherein the second indicator panel is visible through the window when the lancet has been moved to the piercing position and pulled back into the housing.

5. The safety lancet assembly of claim 1, further including a gap formed between the second indicator panel and the window formed within the housing for receiving the first indicator panel.

6. The safety lancet assembly of claim 1, where the first indicator panel is connected to the block.

7. The safety lancet of claim 6, wherein said second indicator panel is connected to said housing.

8. The safety lancet assembly of claim 1, wherein the assembly is a single use device.

9. The safety lancet assembly of claim 1, wherein the piercing tip is a needle.

10. The safety lancet assembly of claim 1, wherein the biasing element comprises a spring attached to the block.

11. The safety lancet assembly of claim 1, further including a removable guard connected to the housing for preventing the accidental release of the actuation assembly, said guard precluding movement of said release tab sufficient to release said lancet prior to removal of said guard from said housing.

12. The safety lancet of claim 11, wherein a portion of said removable guard extends between said release tab and the remainder of said housing such that said release tab is precluded from pivoting.

13. The safety lancet of claim 1, wherein said second indicator panel is connected to said housing.

14. A safety lancet assembly comprising:
    a housing comprising a first end having an opening, a second end, a top surface, an indicator window positioned in said top surface, and an actuation assembly;
    a lancet including a block, a needle extending from said block, said needle having a piercing tip, and a pair of catches positioned on said block;
    the lancet disposed within the housing and operatively aligned to move at least from a retracted position wherein the lancet is completely enclosed by the housing to a piercing position wherein said piercing tip temporarily extends through said opening in said first end of said housing;
    a driving assembly for moving the lancet from the retracted position to the piercing position, said driving assembly comprising a biasing element operatively disposed between the lancet and the housing, wherein said biasing element propels said lancet from the retracted position to the piercing position and then pulls said piercing tip back into the housing such that said lancet is again completely enclosed by the housing;
    said actuation assembly structured to actuate said driving assembly to release the lancet from the retracted position, said actuation assembly being pivotable relative to said top surface of said housing, said actuation assembly comprising in combination a release tab extending outwardly relative to said top surface and a pair of inwardly extending arms, said arms abutting said catches of said block and precluding movement of said lancet from said retracted position until said actuation assembly is activated by pivoting said release tab relative to said top surface of said housing such that said arms pivot away from and no longer abut said catches of said block, thereby allowing said biasing element to move said lancet from said retracted position to said piercing position; and
    a use indicator, said use indicator visually indicating whether said lancet has been released from the retracted position, said use indicator comprising a first indicator panel connected to said block and a second indicator panel connected to said housing, wherein the first and second indicator panels are located directly below said indicator window when the lancet is in the retracted position and the first indicator panel substantially obscures the second indicator panel from view in the window when the lancet is in the retracted position, and wherein when the lancet is released by said actuation assembly from said retracted position and pulled back into said housing such that said lancet is again completely enclosed by the housing said first indicator panel no longer obscures said second indicator panel from view in the window; and wherein after said lancet is released by said actuation assembly from said retracted position and pulled back into said housing such that said lancet is again completely enclosed by the housing, further movement of said lancet by said actuation assembly is precluded.

15. The safety lancet assembly of claim 14, further including a removable guard connected to the housing for preventing the accidental release of the actuation assembly, said guard precluding movement of said release tab sufficient to release said lancet prior to removal of said guard from said housing.

16. The safety lancet of claim 15, wherein a portion of said removable guard extends between said release tab and said top surface of said housing such that said release tab is precluded from pivoting.

17. The safety lancet assembly of claim 14, wherein the surfaces of the first and second indicator panels visible through the indicator window are different colors.

18. The safety lancet assembly of claim 14, wherein the surfaces of the first and second indicator panels visible through the indicator window are distinguishable.

* * * * *